(12) United States Patent
Sivaprakasam (10) Patent No.: US 8,213,010 B2
(45) Date of Patent: Jul. 3, 2012

(54) POLARIZED ELASTIC SCATTER DETECTION METHOD AND SYSTEM OF TRACKING AND MEASURING THE VELOCITY OF INDIVIDUAL AEROSOL PARTICLES

(75) Inventor: Vasanthi Sivaprakasam, Waldorf, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 449 days.

(21) Appl. No.: 12/554,567

(22) Filed: Sep. 4, 2009

(65) Prior Publication Data

US 2012/0105849 A1    May 3, 2012

(51) Int. Cl.
*G01N 21/00* (2006.01)
(52) U.S. Cl. .................... 356/338; 356/339; 356/340
(58) Field of Classification Search ........... 356/335–344
See application file for complete search history.

(56) References Cited

U.S. PATENT DOCUMENTS

| | | | | | |
|---|---|---|---|---|---|
| 4,859,055 | A | * | 8/1989 | Gal et al. | 356/28 |
| 5,608,522 | A | * | 3/1997 | Breda | 356/496 |
| 6,532,067 | B1 | * | 3/2003 | Chang et al. | 356/318 |
| 7,057,712 | B2 | * | 6/2006 | Beck et al. | 356/72 |
| 7,126,687 | B2 | * | 10/2006 | Hill et al. | 356/336 |
| 7,339,671 | B2 | * | 3/2008 | Peng | 356/338 |
| 7,416,902 | B2 | * | 8/2008 | Pletcher et al. | 436/174 |
| 8,047,053 | B2 | * | 11/2011 | Call et al. | 73/28.01 |
| 8,072,584 | B2 | * | 12/2011 | Caldwell et al. | 356/28.5 |

OTHER PUBLICATIONS

Jay D. Eversole, Vasanthi Sivaprakasam, Timothy A. Pletcher, and D. Keller, Single aerosol particle selection and capture using laser scattering and fluorescence, Proceedings of SPIE, Sep. 16-17, 2008, vol. 7116.

Jay D. Eversole, Vasanthi Sivaprakasam, Timothy A. Pletcher, and D. Keller, Single aerosol particle selection and capture using laser scattering and fluorescence, JDE, Aug. 7, 2009.

Vasanthi Sivaprakasam, Timothy A. Pletcher, John E. Tucker, Alan L. Huston, Joseph McGinn, David Keller and Jay D. Eversole, Classification and selective collection of individual aerosol particles using laser-induced fluorescence, Applied Optics, Feb. 1, 2009, vol. 48, No. 4.

* cited by examiner

*Primary Examiner* — Kara E Geisel
*Assistant Examiner* — Jarreas C Underwood
(74) *Attorney, Agent, or Firm* — Amy L. Ressing; John L. Young (57) ABSTRACT

Measuring and tracking velocity of individual aerosol particles in a bio-threat detection system are accomplished using a single beam laser source in combination with a birefringent crystal that splits the laser beam into two beams having orthogonal polarization. Scattered light is collected with an elliptical reflector and directed into two detection channels, sampling total elastic scatter in the first channel and sampling polarized elastic scatter in the second channel. The difference in intensity of the scattered light in the polarized channel is used to identify the position of the particles. By taking the ratio of signal output from the polarized detector to the total scatter detector, a threshold level can be established to determine the presence of particles traversing the two beams. The particles are time stamped as they traverse the two beams and the time difference between the pulses can be used to measure the velocity of the particles.

13 Claims, 9 Drawing Sheets

```
BIOLOGICAL-THREAT DETECTION
SYSTEM 100
```

```
┌─────────────────┐     ┌─────────────────┐     ┌─────────────────────┐
│ FRONT END       │     │ AEROSOL PARTICLE│     │ DATA ANALYSIS,      │
│ AEROSOL PARTICLE├─────┤ INTERROGATOR    ├─────┤ INSTRUMENT TIMING,  │
│ CONCENTRATOR    │     │ MODULE 104      │     │ SYSTEM CONTROL      │
│ SUBSYSTEM 102   │     │                 │     │ SUBSYSTEM 108       │
└─────────────────┘     └─────────────────┘     └──────────┬──────────┘
                                                           │
                                                ┌──────────┴──────────┐
                                                │ BIO-THREAT AEROSOL  │
                                                │ PARTICLE COLLECTOR  │
                                                │ SUBSYSTEM 106       │
                                                └─────────────────────┘
```

```
                    ┌─────┐
                    │  A  │ 410
                    └──┬──┘
                       ▼                                    412
┌──────────────────────────────────────────────────────┐
│  INTERROGATING, USING FLUORESCENCE TO CLASSIFY,       │
│  EACH AEROSOL PARTICLE TRAVERSING TOP AND BOTTOM      │
│                      BEAMS:                           │
│                                                       │
│   ┌───────────────────────────────────────────────┐   │
│   │   ALIGNING INTERROGATOR BEAMS        414      │   │
│   └───────────────────┬───────────────────────────┘   │
│                       ▼                               │
│   ┌───────────────────────────────────────────────┐   │
│   │   EXCITING FLUORESCENCE WITH TWO UV           │   │
│   │   INTERROGATOR BEAMS                 416      │   │
│   └───────────────────┬───────────────────────────┘   │
│                       ▼                               │
│   ┌───────────────────────────────────────────────┐   │
│   │   COLLECTING SCATTERED LIGHT         418      │   │
│   └───────────────────┬───────────────────────────┘   │
│                       ▼                               │
│   ┌───────────────────────────────────────────────┐   │
│   │   DIRECTING COLLECTED LIGHT INTO              │   │
│   │   DETECTOR CHANNELS                  420      │   │
│   └───────────────────┬───────────────────────────┘   │
│                       ▼                               │
│   ┌───────────────────────────────────────────────┐   │
│   │   SAMPLING TOTAL ELASTIC SCATTER     422      │   │
│   └───────────────────┬───────────────────────────┘   │
│                       ▼                               │
│   ┌───────────────────────────────────────────────┐   │
│   │   SAMPLING POLARIZED ELASTIC SCATTER IN       │   │
│   │   THE SECOND DETECTOR CHANNEL        424      │   │
│   └───────────────────┬───────────────────────────┘   │
│                       ▼                               │
│   ┌───────────────────────────────────────────────┐   │
│   │   IDENTIFYING WHEN AEROSOL PARTICLES          │   │
│   │   ARE TRAVERSING BEAMS               426      │   │
│   └───────────────────────────────────────────────┘   │
└──────────────────────┬────────────────────────────────┘
                       ▼                    428
                    ┌─────┐
                    │  B  │
                    └──┬──┘
                       ▼                         FIG. 4B
```

```
                    ┌──────┐
                    │  B   │── 428
                    └──┬───┘
                       ▼
    ┌─────────────────────────────────────┐
    │   OUTPUTTING SIGNALS FROM THE       │── 430
    │ DETECTOR CHANNELS TO THE COMPUTER   │
    └─────────────────┬───────────────────┘
                      ▼
    ┌─────────────────────────────────────┐
    │ DETERMINING A RATIO OF THE POLARIZED│── 432
    │ SCATTER TO THE TOTAL ELASTIC SCATTER│
    └─────────────────┬───────────────────┘
                      ▼
    ┌─────────────────────────────────────┐
    │      ESTABLISHING A THRESHOLD FOR   │── 434
    │ DETERMINING IF A PARTICLE IS PRESENT IN │
    │   THE TOP BEAM OR THE BOTTOM BEAM   │
    └─────────────────┬───────────────────┘
                      ▼
    ┌─────────────────────────────────────┐
    │ TIME STAMPING AND ASSIGNING VELOCITY│── 436
    │ TO EACH PARTICLE TRAVERSING TOP AND │
    │            BOTTOM BEAMS             │
    └─────────────────┬───────────────────┘
                      ▼
    ┌─────────────────────────────────────┐
    │      PERFORMING DATA ANALYSIS,      │── 438
    │ INSTRUMENT TIMING, SYSTEM CONTROL   │
    │             FUNCTIONS               │
    └─────────────────┬───────────────────┘
                      ▼
    ┌─────────────────────────────────────┐
    │    COLLECTING BIO-THREAT AEROSOL    │── 440
    │ PARTICLES IN THE BIO-THREAT AEROSOL │
    │         PARTICLE COLLECTOR          │
    └─────────────────┬───────────────────┘
                      ▼
                ┌───────────┐
                │RETURN/END │── 442
                └───────────┘
```

FIG. 4C

. Screenshot of the FPGA showing the total and polarized elastic scatter signal and the ratio of the polarized to total scatter

POLARIZED ELASTIC SCATTER DETECTION METHOD AND SYSTEM OF TRACKING AND MEASURING THE VELOCITY OF INDIVIDUAL AEROSOL PARTICLES

FIELD OF THE INVENTION

The present invention relates to chemical and biological agent detection methods and systems, regarding defense of cities, large bases, civilian personnel and military forces against chemical, biological, or radiological (CBR) incidents and/or attacks involving toxins, viruses, bacteria and/or general airborne pathogenic biological aerosols, but can also be applied to ambient aerosol particles or pollutants and/or contaminants. More particularly, the present invention applies to detecting the position of one or more particles and identifying a pair of pulses corresponding to each of the one or more particles, in order to track the particles and measure the velocity of the particles reliably and reducing false alarms in detection and threat analysis.

BACKGROUND OF THE INVENTION

In addressing concerns about bioterrorism and bio-warfare there has been significant activity in recent years towards development of new sensors to detect the presence of pathogenic biological aerosols. How ever, the detection and positive identification of bio-agent particles in the air presents many challenges. Ideally, detection systems should be capable of rapidly detecting and confirming bio-agents at low concentrations with high detection (true positive) probability but simultaneously with low false positive probability. Therefore, detection assays should be sensitive and specific, capable of detecting low concentrations of target agents without interference from background materials. However, these requirements have proved difficult to achieve, employing biological-threat detection systems in efforts to process real world samples. In typical atmospheric environments, the number density of ambient aerosol particles frequently becomes large enough to easily mask the presence of a minor subpopulation of a biological aerosol at concentrations of concern. In collecting aerosol samples, the presence of ambient background particles creates a complex matrix material that can interfere with, or inhibit, biological detection/identification assays. There is overwhelming evidence that the sensitivity, speed of detection, and levels of misclassification of detection systems are compromised when the systems are presented with air samples containing dust from a variety of environments. The failure of polymerase chain reaction (PCR) analysis to correctly identify and quantify the number of targets for a given experiment has caused researchers to explore a variety of sample processing steps as a means to remove the inhibiting factors prior to running the identification assay. Such preprocessing includes sample dilution, DNA capture onto magnetic beads, and development and use of special reagents such as Gene Releaser. Each of these sample preparation methods has a significant cost associated with its use as well as adding time and complexity to the detection system.

Generic biological-threat detection systems employ modules and/or subsystems composed of concentrator subsystems, interrogator subsystems, and sample collector subsystems. These generic biological-threat detection systems are compatible and combinable with a wide variety of specific biological sample detection modules and/or subsystems.

Laser-induced fluorescence (LIF) in the ultraviolet (UV) spectral region has been used in front-end trigger sensor modules for detecting bio-threat agents. UV-LIF systems can be operated autonomously and continuously and are efficient in differentiating biological from non-biological particle compositions. However, discrimination among biological organisms has been typically limited to large classes (fungal/bacterial/viral, for ex ample) and has not shown sufficient specificity to reach the level of speciation. Modules, systems and/or subsystems employing multiple-wavelength excited fluorescence have shown improved discrimination capabilities compared to single-wavelength excitation systems. The feasibility of using fluorescence and scattering signatures to classify individual aerosol particles on-the-fly in order to separate and collect selected particles has been previously explored using a pulse, or jet, of air to deflect selected particles and collect them in a different spatial region, enabling separation and classification at a rate of only about 300 Hz.

The ability to accurately measure the velocity and track the position of individual particles for on-the-fly classification and selective capture is essential for next-generation chemical and biological agent detection systems. Velocity of a particle can be determined by measuring the transit time between two parallel light beams of known spacing by detecting the scattered light pulses with a photoelectric detector such as a photomultiplier tube (PMT). The accuracy of the measurement improves with increasing separation between the two beams until the particle throughput rate becomes so large that it becomes difficult to keep track of the individual particles. If two or more particles enter the measurement zone before the first particle has traveled through both beams, then it can be difficult to assign which light scattering event is associated with which particle. To track the particle and measure the velocity reliably we need to be able to detect the position of the particle and identify the pair of pulses that correspond to each particle.

One approach to overcome this problem is to use two separate beams from different laser sources, operating at two different wavelengths. In this way, the signals from the two beams can be easily distinguished. Problems with this approach include the mechanical stability of the optical mounts and the pointing stability of the two laser sources, any small change in the positions of the beams will result in error in the velocity measurement. The requirement of the use of two lasers also adds to the expense and complexity of the system.

The need exists for the ability to detect and classify individual aerosols in real time.

Furthermore, the need exists for the ability to enrich the concentration of suspected threat particles by sorting and collecting aerosols based on their classification, thus improving the reliability of the threat analysis and reduce the frequency of false alarms.

Further, the need exists for methods and systems that reduce or eliminate the problems involving particle through put rate becoming so large that it becomes difficult to assign which light scattering event is associated with which particle.

Further the need exists for the ability to detect the position of the particle and identify the pair of pulses that correspond to each particle.

In addition, the need exists for overcoming problems introduced by using two separate beams from different laser sources, such problems include problems of mechanical stability of the optical mounts and the pointing stability of the two laser sources.

Further, the need exists for reducing the expense and complexity of using multiple lasers in velocity measurements of particles.

SUMMARY OF THE INVENTION

A module, and/or subsystem of a biological-threat detection system, and method including instructions implemented using computer readable and computer executable program code executed on a computer processor implemented in conjunction with optical components cooperate in a polarized elastic scatter detection method and system of tracking and measuring the velocity of aerosol particles. The polarized elastic scatter detection method and system of tracking and measuring the velocity of aerosol particles is implemented as a depolarization velocimetric system with components including a single laser source, such as a diode laser for interrogating aerosol particles. After concentrating aerosol particles in a front end aerosol particle concentrator subsystem, the concentrated aerosol particles are interrogated by an aerosol particle interrogator module, where the diode laser of the depolarization velocimetric system is focused, using a cylindrical lens, to form a sheet beam at the focal volume of an elliptical collection optic reflector. The sheet beam is split into two separate orthogonally polarized sheet beams using a birefrigent crystal, where the top beam is S-polarized and the bottom beam is P-polarized. Separation between the two beams is determined by the length of the crystal. Elastic scattered light from the aerosol particles is collected, in an interrogation chamber, by the elliptical collection optic reflector. The collected elastic scattered light is directed into two detector channels using a beam splitter and is focused onto two photomultiplier tube (PMT) detectors. One detector channel samples the total elastic scatter and the other detector channel samples elastic scatter polarized in the S direction. The polarizer is oriented perpendicular to the bottom P-polarized beam and the measured elastic scatter intensity is relatively weak compared to the elastic scatter measured for the top beam. The difference in intensity of the scattered light in the detector channel that samples elastic scatter polarized in the S direction is used to identify when a particle is traversing through the top and the bottom beams. The magnitude of the signals in the total elastic scatter channel can be balanced between the two polarizations. By taking the ratio of the signal output from the detector channel that samples elastic scatter polarized in the S direction (i.e., the polarized detector channel) to the total intensity detector, a threshold level can be established to determine if the particle is present in the top beam or the bottom beam. A window function can be established to match pairs of pulses from the same particle and the time difference between the pulses can be used to measure the velocity of the particle.

DETAILED DESCRIPTION

Preferred exemplary embodiments of the present invention are now described with reference to the figures, in which like reference numerals are generally used to indicate identical or functionally similar elements. While specific details of the preferred exemplary embodiments are discussed, it should be understood that this is done for illustrative purposes only. A person skilled in the relevant art will recognize that other configurations and arrangements can be used without departing from the spirit and scope of the preferred exemplary embodiments. It will also be apparent to a person skilled in the relevant art that the exemplary embodiments can also be employed in other applications. Further, the terms "a", "an", "first", "second" and "third" etc. used herein do not denote limitations of quantity, but rather denote the presence of one or more of the referenced items(s).

Figure 1:
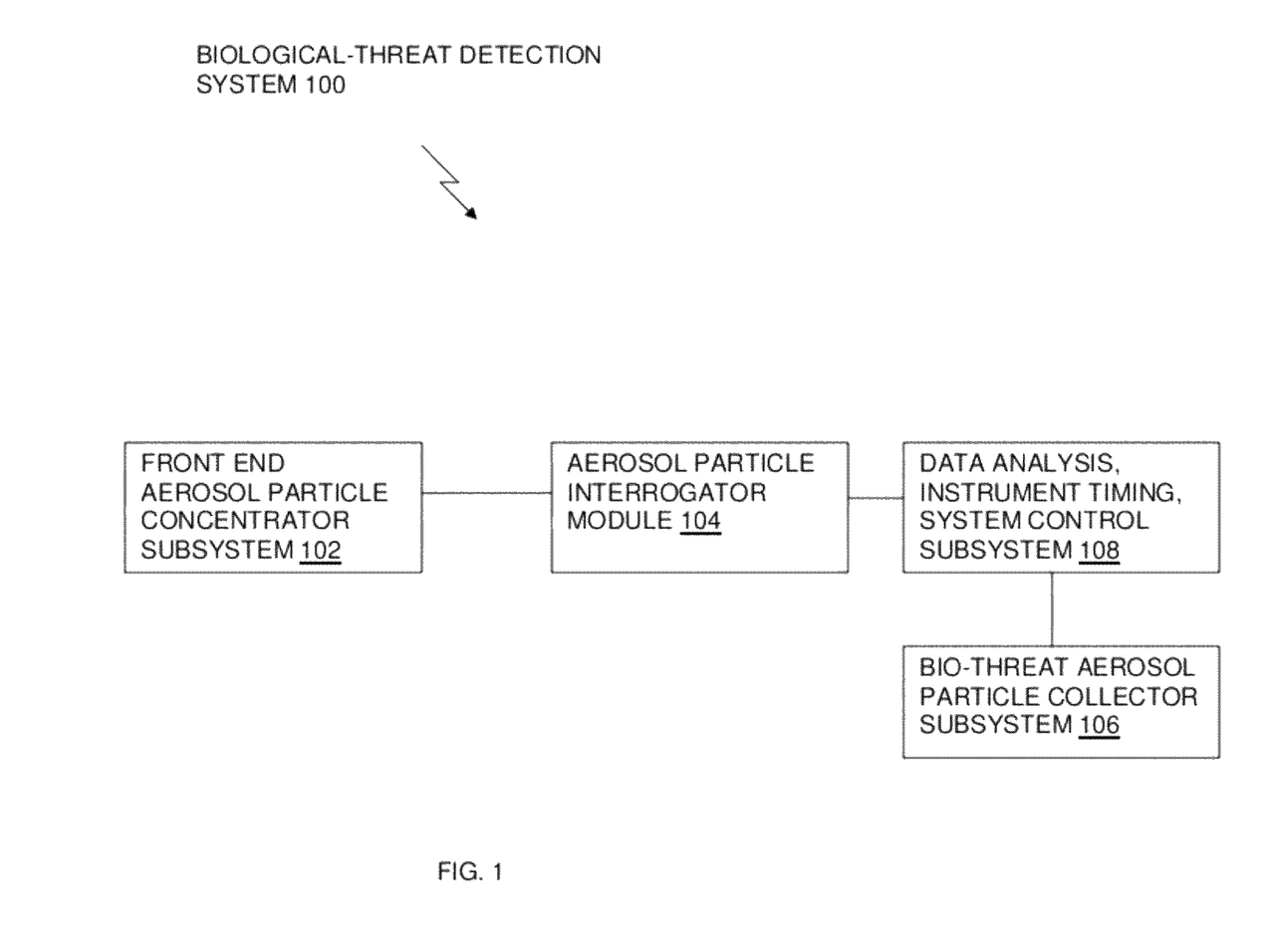
FIG. 1 illustrates a generic bio-threat detection system (System 100).

FIG. 1 describes a system for tracking and measuring aerosol particles in a biological-threat detection system 100 (hereafter "the system 100"). The system 100 includes a front end aerosol particle concentrator subsystem 102 (hereafter "the subsystem 102"), which is communicatively coupled to a bio-threat aerosol particle collector subsystem 106 (hereafter "the subsystem 106") through an aerosol particle interrogator module 104 (hereafter "the module 104"). Furthermore, the subsystem 106 is communicatively coupled to a data analysis, instrument timing, and system control subsystem 108 (hereafter "the subsystem 108").

Figure 2:
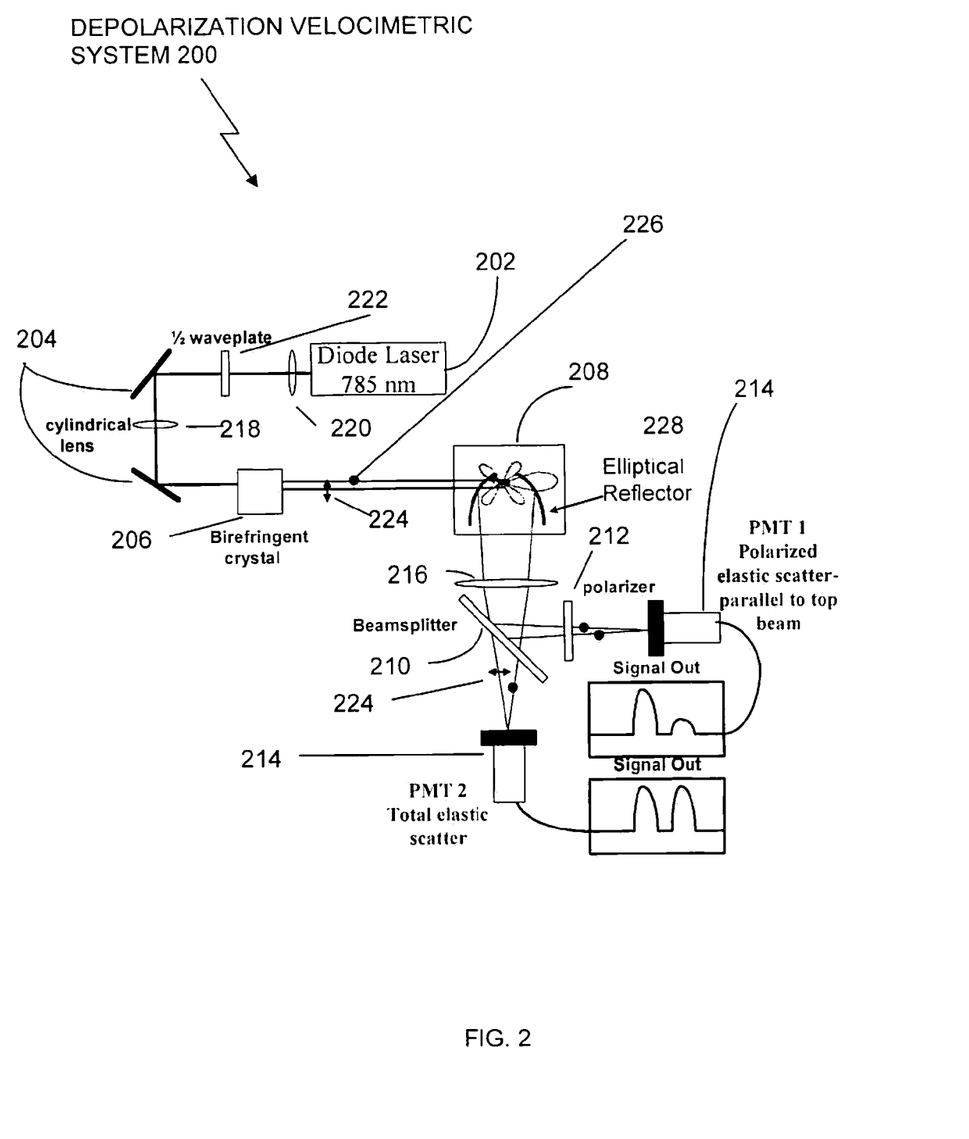
FIG. 2 illustrates a depolarization velocimetric system (System 200) which can be integrated as a subsystem with the system 100.
Figure 3:
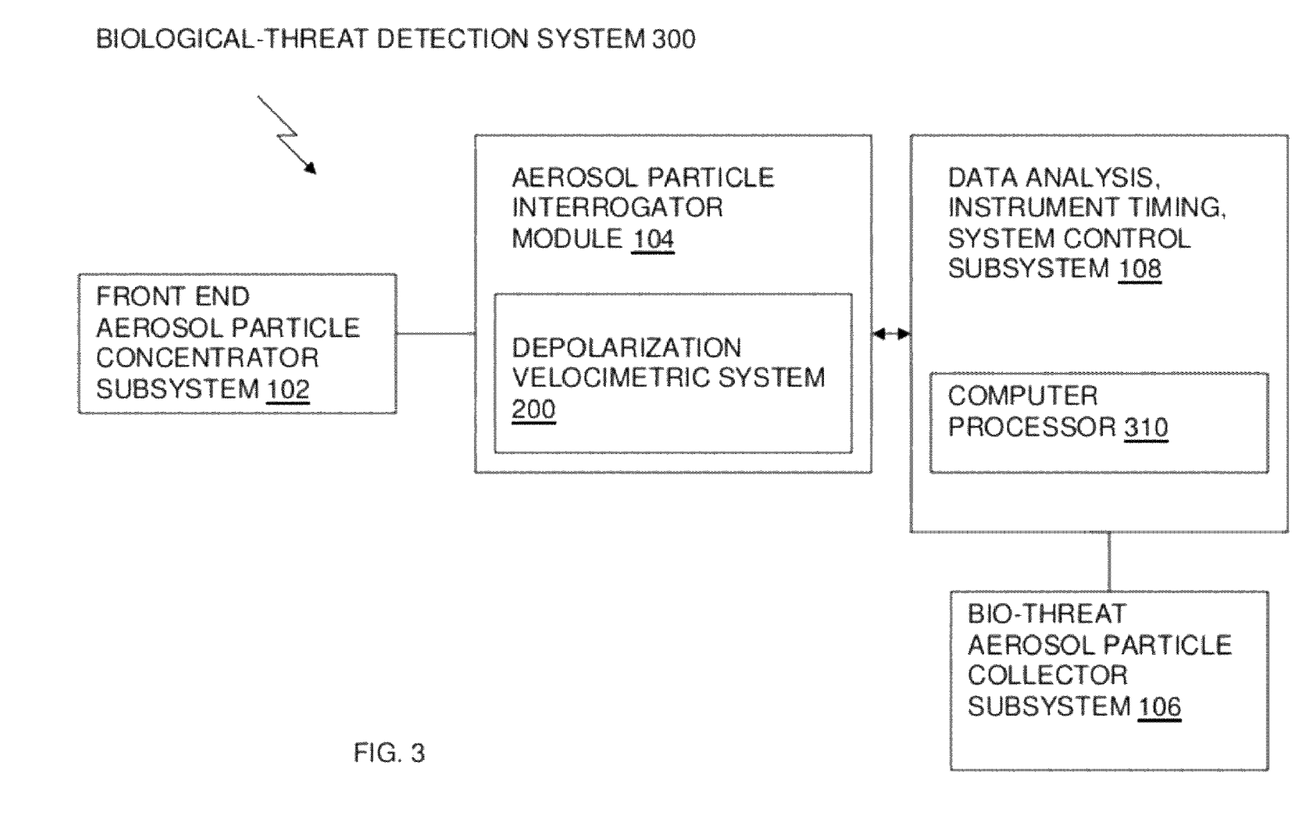
FIG. 3 illustrates a bio-threat detection system implementing the depolarization velocimetric system.
Figure 4A:
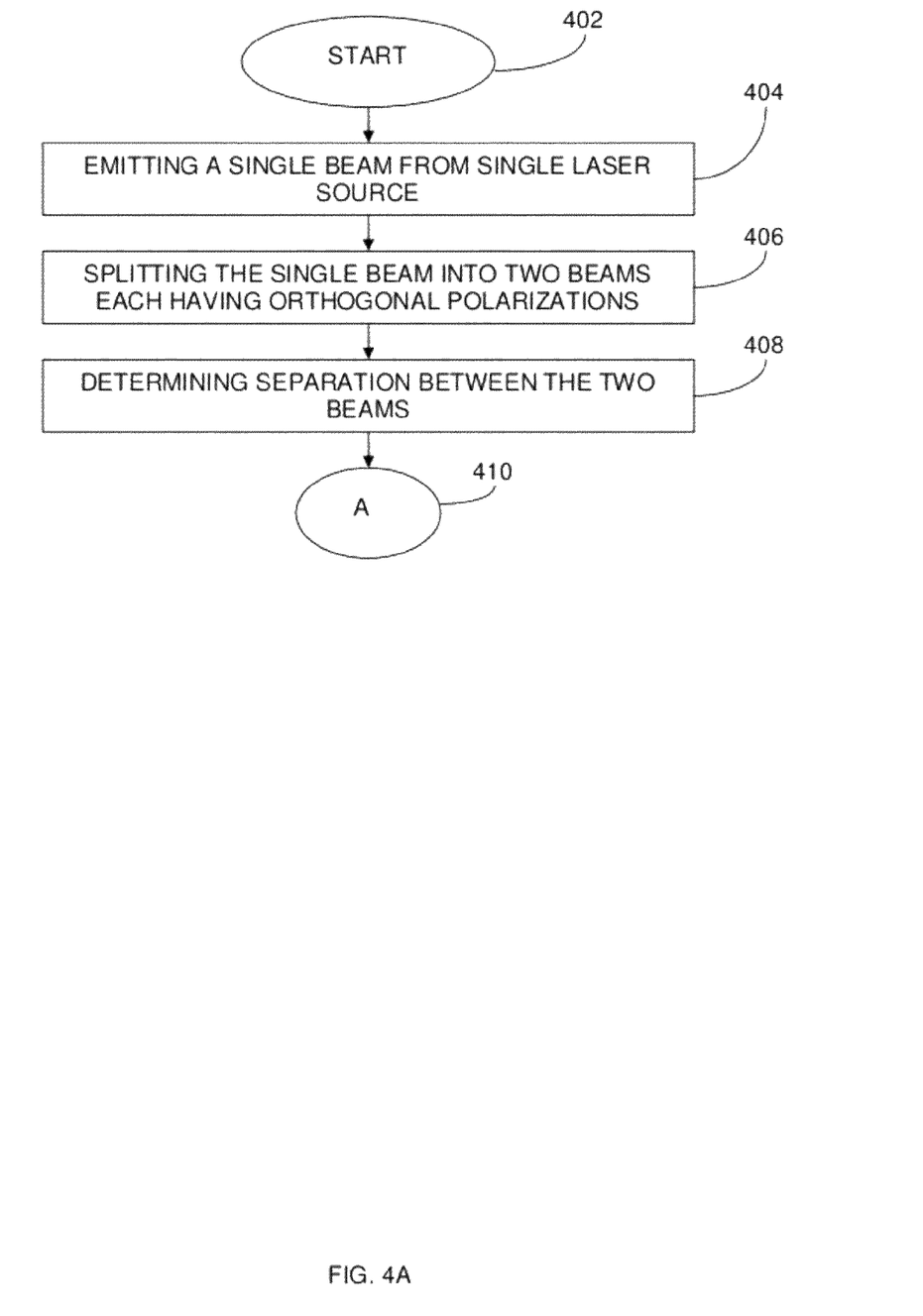
FIG. 4A illustrates elements of a method of operation of the depolarization velocimetric system in the bio-threat detection system.
Figure 4B:
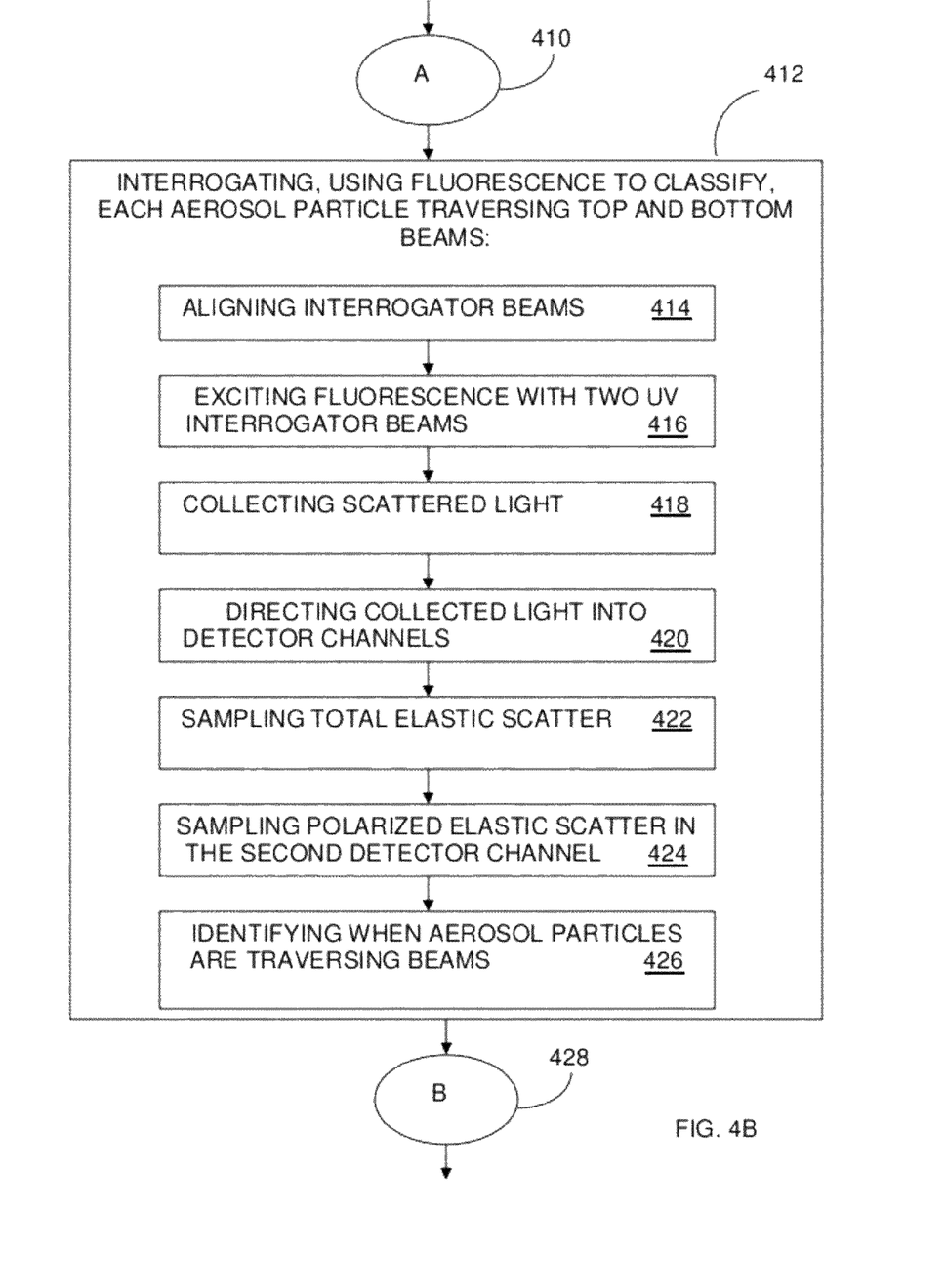
FIG. 4B further illustrates elements of the method of operation of the depolarization velocimetric system in the bio-threat detection system.
Figure 4C:
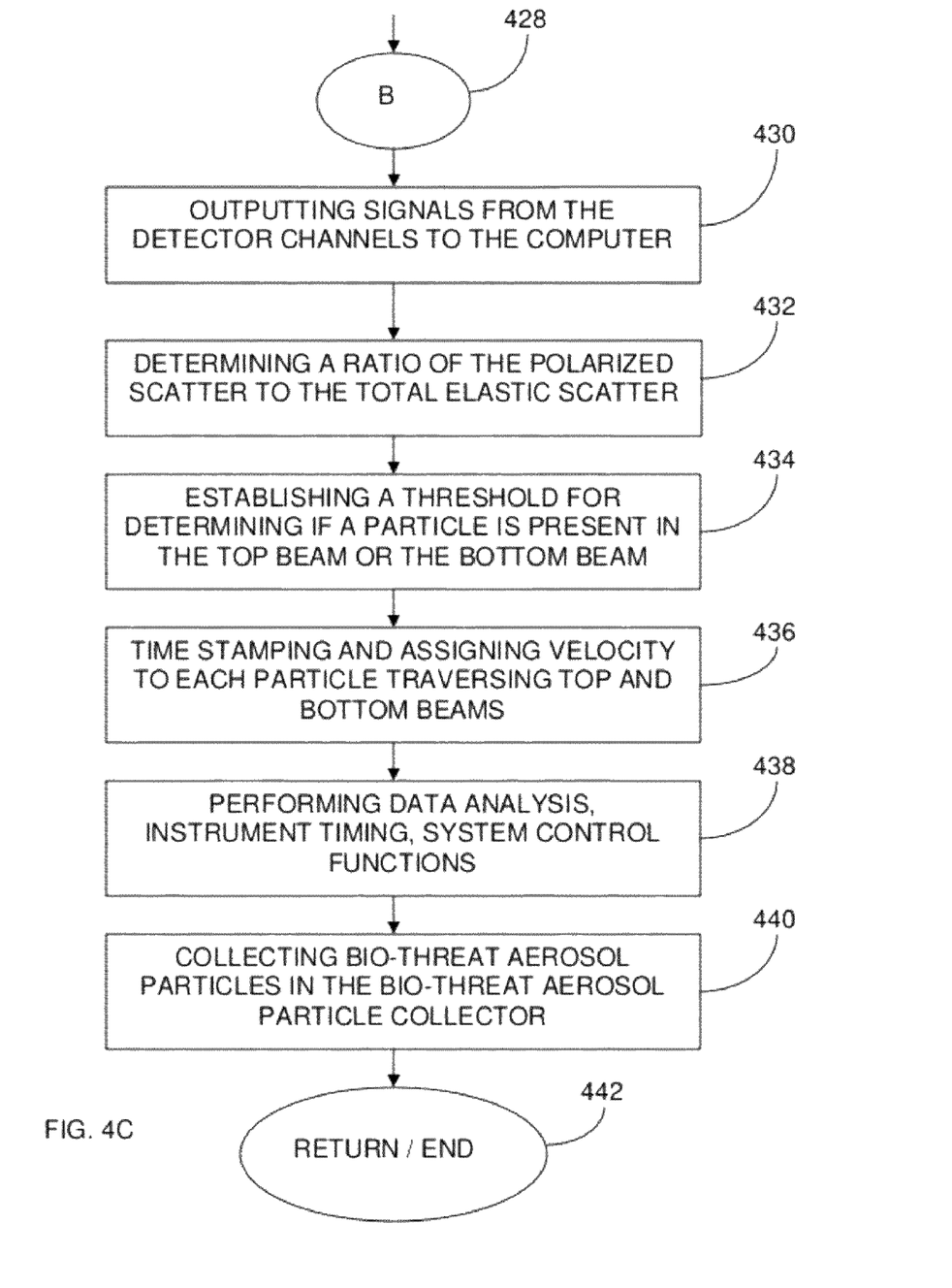
FIG. 4C further illustrates the method of operation of the depolarization velocimetric system implemented in the bio-threat detection system.
Figure 5:
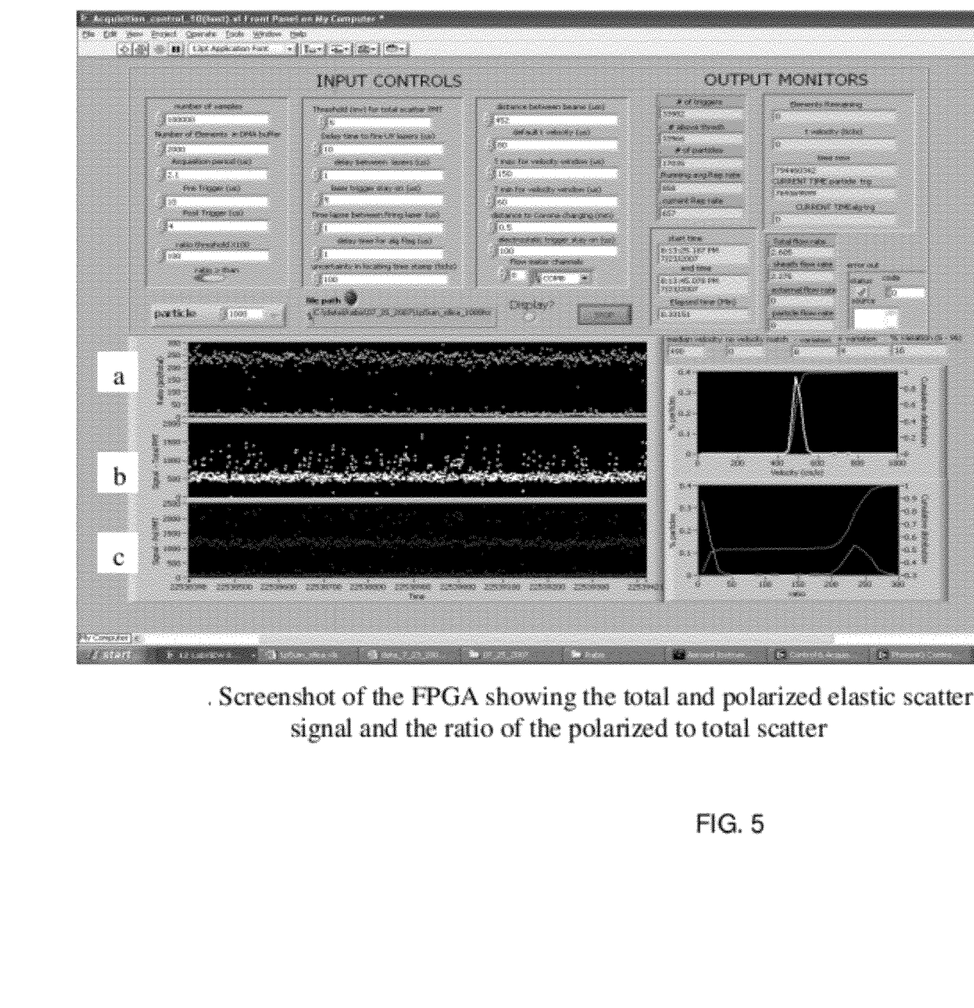
FIG. 5 is a screenshot of a field programmable gate array showing the total and polarized elastic scatter signal and the ratio of the polarized to total scatter.
Figure 6:
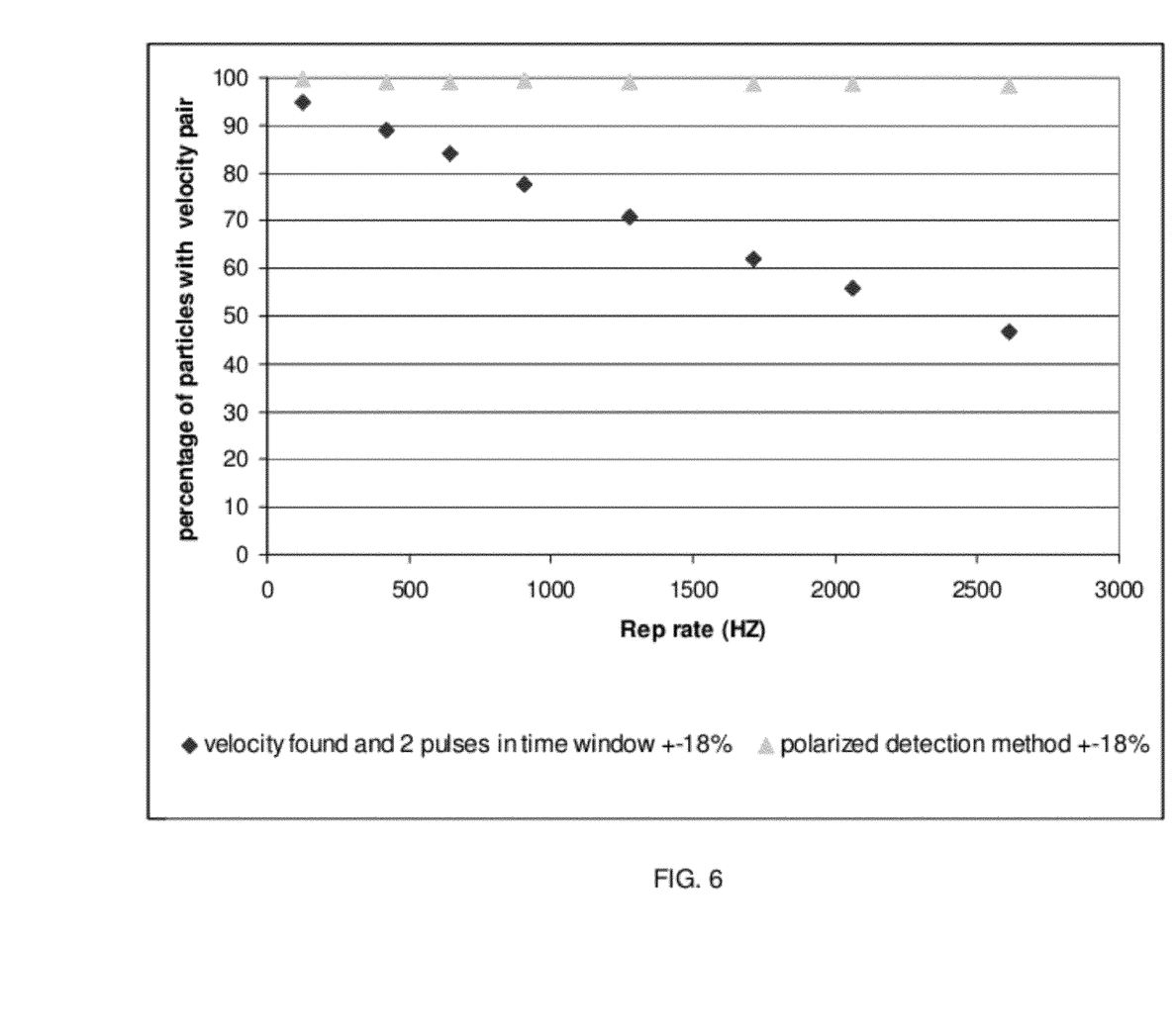
FIG. 6 illustrates statistics of finding a velocity pair for the polarization and traditional techniques. Data analyzed include mono-dispersed particles of varying rep rate.
Figure 7:
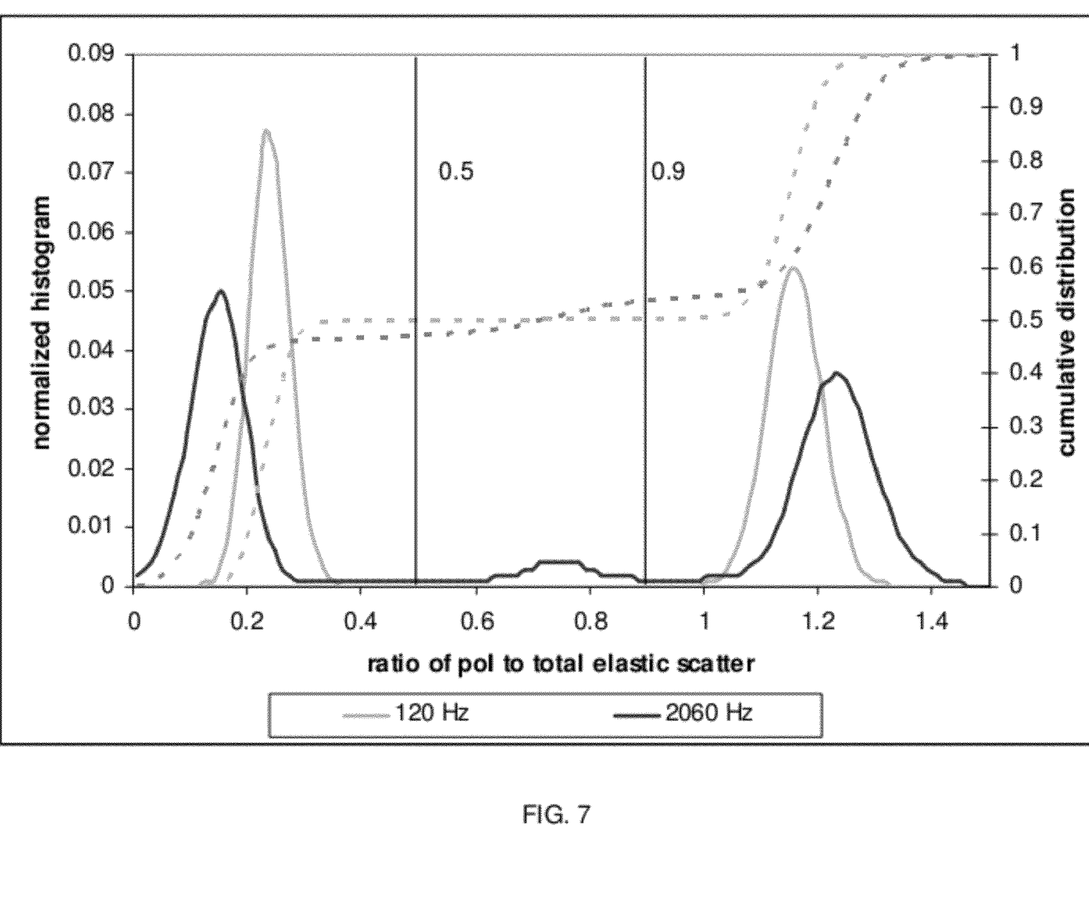
FIG. 7A illustrates a plot of a Histogram and cumulative distribution of the ratio of the polarized to total scatter intensity measured for particles flowing at 2 different throughputs, i.e., rates of 120 Hz and 2060 Hz.

Referring to FIG. 2, FIG. 3 and FIG. 4, exemplary embodiments describe tracking and measuring the velocity of aerosol particles in a biological-threat detection system 300 (hereafter "the system 300") including of instructions implemented using computer readable and computer executable program code executed on a computer processor, such as the computer processor 310, implemented in conjunction with optical components described herein, cooperate in tracking and measuring the velocity of aerosol particles. The system 300, in a manner similar to the system 100 (see FIG. 1) includes a front end aerosol particle concentrator subsystem, such as the subsystem 102, which is communicatively coupled to a bio-threat aerosol particle collector subsystem, such as the subsystem 106, through an aerosol particle interrogator module, such as the module 104 and the data analysis, instrument timing, and system control subsystem, such as the subsystem 108. Furthermore, the data analysis, instrument timing, and system control subsystem, such as the subsystem 108, which is communicatively coupled to the computer processor 310. Thus, the subsystem 106 can be characterized as an electrostatic capture mechanism used to deposit individual potential bio-threats particles onto a stainless steel substrate while particles that are not classified as targets are discharged with the exiting airflow.

In addition, in exemplary embodiments, the system 300 includes a depolarization velocimetric system 200, (hereafter "the system 200") implementing a depolarization velocimetric method 400 (hereafter "the method 400"). The system 200 can also be characterized as a depolarization measurement system for determining aerosol particle velocity.

Referring to FIG. 2, FIG. 3 and FIG. 4, in exemplary embodiments, after concentrating aerosol particles in a front end aerosol particle concentrator subsystem, such as the subsystem 102, the concentrated aerosol particles are interrogated by an aerosol particle interrogator module, such as the module 104, which includes the system 200.

Again referring to FIG. 2, FIG. 3 and FIG. 4, in exemplary embodiments, the system 200 can be characterized as a module and/or subsystem having components including a single laser source, such as a diode laser 202 for interrogating aerosol particles.

According to exemplary embodiments, the diode laser 202 emits a single beam for interrogating aerosol particles and is communicatively coupled, through a first lens 220, to a one-half waveplate 222, through which the single beam is reflected by a first mirror 204 through a cylindrical lens 218. The cylindrical lens 218 is focused to form a sheet beam with dimensions of about 70 micrometers by 3 millimeters at a focal volume of an elliptical collection optic. The 70 micrometer by 3 millimeter sheet beam is reflected by a second mirror 204 to a birefringent crystal 206, which splits the 70 micrometer by 3 millimeter sheet beam into two orthogonally polarized beams separated by about 350 micrometers. The separation between the two beams is determined by the length of the birefringent crystal 206 and is not sensitive to small beam pointing errors.

According to exemplary embodiments, a first beam of the two orthogonally polarized beams is a top beam and is an S-polarized beam 226 (hereafter "the S-polarized beam 226"). A second beam of the two orthogonally polarized beams is a bottom beam and is a P-polarized beam 224 (hereafter "the P-polarized beam 224"). Both the S-polarized beam 226 and the P-polarized beam 224 are emitted into an interrogation chamber 208 (hereafter "the interrogation chamber 208").

In exemplary embodiments, the interrogation chamber 208 includes an elliptical collection optic reflector 228, which collects elastic scattered light from aerosol particles interrogated by the S-polarized beam 226 and the P-polarized beam 224. The elliptical collection optic reflector 228 has a collection efficiency of over 2π steradians.

A third lens 216 focuses the elastic scattered light to be directed into detector channels.

Further according to exemplary embodiments, a beam splitter 210 splits elastic scattered light into a first detector channel 214 and a second detector channel 214. The first and second detector channels each comprise a photomultiplier tube (PMT) and the first detector channel is hereafter referred to as "the first detector channel 214 (PMT1)". The second detector channel is hereafter referred to as "the second detector channel 214 (PMT2)".

The beam splitter 210 directs elastic scattered light through a polarizer 212, causing S-polarized beam 226 (i.e., the beam having S-Polarization) to be sampled by the first detector channel 214 (PMT1). The polarizer 212 is oriented perpendicular to the bottom P-polarized beam 224 (i.e., the beam(s) having P-Polarization) and the measured elastic scatter intensity is relatively weak compared to the elastic scatter measured for the top beam.

Further, the beam splitter 210 directs total elastic scattered light to be sampled by the second detector channel 214 (PMT2).

Signals from the first detector channel 214 (PMT1) and the second detector channel 214 (PMT2) are outputted to and received from the computer processor 310 for purposes of performing data analysis, instrument timing and system control operations.

Referring to FIG. 2, FIG. 3, FIG. 4A, FIG. 4B and FIG. 4C, according to exemplary embodiments, the method 400 performs the following described operations, pertaining to bio-threat detector using fluorescence interrogation applications to classify particles traversing top and bottom laser beams in a depolarization velocimetric module having a diode laser source and computer automated instrumentation.

At an operation start 402 (hereafter "the operation 402"), the method 400 and the system 300 are activated electronically.

Referring again to FIG. 2, FIG. 3, FIG. 4A, FIG. 4B and FIG. 4C, according to exemplary embodiments, at the operation emitting a single beam from a single laser source 404 (hereafter "the operation 404"), after aerosol particles are concentrated by the front end aerosol particle concentrator subsystem 102, the concentrated aerosol particles are received by the module 104, and acted upon by the system 200, where the diode laser 202 emits a single beam for interrogating aerosol particles and is communicatively coupled, through a first lens 220, to a one-half waveplate 222, through which the single beam is reflected by a first mirror 204 through a cylindrical lens 218. The cylindrical lens 218 is focused to form a 70 micrometer by 3 millimeter sheet beam at a focal volume of an elliptical collection optic.

At an operation splitting the single beam into two beams each having orthogonal polarizations 406 (hereafter "the operation 406"), the 70 micrometer by 3 millimeter sheet beam is reflected by a second mirror 204 to a birefringent crystal 206, which splits the 70 micrometer by 3 millimeter sheet beam into two orthogonally polarized beams separated by 350 micrometers. The first beam of the two orthogonally polarized beams is a top beam and is the S-polarized beam 226. The second beam of the two orthogonally polarized beams is the bottom beam and is the P-polarized beam 224.

Referring to FIG. 4A, at an operation determining separation between the two beams 408 (hereafter "the operation 408"), the technique of splitting the beam into two beams ensures that the alignment and the separation between the two beams is preserved, which is vital in measuring the velocity of the particles accurately. Separation between the two beams is determined by the length of the birefringent crystal 206 and is not sensitive to small beam pointing errors.

Referring to FIG. 4A and FIG. 4B, the oval labeled "A" (410) in FIG. 4A corresponds with the oval labeled "A" (410) in FIG. 4B and indicates that the operations of the method 400 from FIG. 4A continue at the oval labeled "A" (410) in FIG. 4B.

Referring to FIG. 4B, at an operation interrogating using fluorescence to classify each aerosol particle traversing top and bottom beams 412 (hereafter "the operation 412"), concentrated aerosol particles are interrogated by the module 104. The module 104 includes the interrogation chamber 208, having the elliptical collection optic reflector 228. In exemplary embodiments, elastic scattered light from the aerosol particles is collected, in an interrogation chamber 208, by the elliptical collection optic reflector 228, such as the elastic scattered light from aerosol particles interrogated by the S-polarized beam 226 and the P-polarized beam 224. The elliptical collection optic reflector 228 has a collection efficiency of over $2\pi$ steradians. Thus, the operation 412 includes several sub-operations, such as a sub-operation of aligning interrogator beams 414, a sub-operation of exciting fluorescence with two UV interrogator beams 416, a sub-operation of collecting scattered light 418, a sub-operation of directing collected light into detector channels 420, a sub-operation of sampling total elastic scatter 422, a sub-operation of sampling polarized elastic scatter 424, and a sub-operation of identifying when aerosol particles are traversing beams 426 (hereafter "the operation 426"); this identifying operation 426 contains several operations and/or sub operations, including outputting signals from the detector channels 214 to the computer processor 310 (see the operation 430); determining a ratio of the polarized scatter to the total elastic scatter (see the operation 432); establishing a threshold for determining if a particle is present in the top and/or bottom beam (see the operation 434); and time stamping and assigning velocity to each particle traversing the beams (see the operation 436).

Referring to FIG. 2, FIG. 3, FIG. 4A, FIG. 4B and FIG. 4C, at the sub-operation aligning interrogator beams 414 (hereafter "the operation 414"), a group of at least two laser-induced fluorescence (LIF) interrogator beams are aligned, for detecting bio-threat agents (these beams can be ultraviolet (UV) excited beams. The alignment of the beams is determined by the characteristics the birefringent crystal 206, based on the technique of splitting the single beam emitted by the diode laser 202 into two beams by the birefringent crystal 206, which ensures that the alignment and the separation between the two beams is preserved.

Referring to FIG. 2, FIG. 3, FIG. 4A, FIG. 4B and FIG. 4C, at the sub-operation exciting fluorescence with two UV interrogator beams 416 (hereafter "the operation 416"), the group of at least two laser-induced fluorescence (LIF) beams use ultraviolet UV interrogator beams employing multiple-wavelength excited fluorescence for determining scattering signatures to classify individual aerosol particles on-the-fly in order to separate and collect selected particles.

Characteristics of UV laser pulses used to excite fluorescence elements include a system and/or subsystem or module having 266 nm and 355 nm laser pulses to sequentially excite single aerosol particles. This type of implementation has been shown to provide significant discrimination between biological and ambient as well as differentiation among classes of biological particles.

Referring again to FIG. 2, FIG. 3, FIG. 4A, FIG. 4B and FIG. 4C, at the sub-operation collecting scattered light 418 (hereafter "the operation 418"), as described in the operation 406, the sheet beam is split into two separate orthogonally polarized sheet beams using the birefringent crystal 206, where the top beam is S-polarized and the bottom beam is P-polarized. Elastic scattered light emitted from the aerosol particles (such as the elastic scattered light from aerosol particles interrogated by the S-polarized beam 226 and the P-polarized beam 224) is collected, in an interrogation chamber 208, by the elliptical collection optic reflector 228.

Referring again to FIG. 2, FIG. 3, FIG. 4A, FIG. 4B and FIG. 4C, at the sub-operation directing collected light into detector channels 420 (hereafter "the operation 420"), collected elastic scattered light is directed into two detector channels. The third lens 216 focuses the elastic scattered light to be directed into detector channels. The beam splitter 210 directs elastic scattered light through a polarizer 212 causing S-polarized beam(s) 226 (i.e., the beam having S-Polarization) to be sampled by the first detector channel 214 (PMT1).

Further, the beam splitter 210 directs total elastic scattered light to be sampled by the second detector channel 214 (PMT2).

Referring again to FIG. 2, FIG. 3, FIG. 4A, FIG. 4B and FIG. 4C, at the sub-operation sampling total elastic scatter 422 (hereafter "the operation 422"), total elastic scattered light (i.e., both the P-Polarized light and the S-Polarized light directed by the beam splitter 210) are sampled by the second detector channel 214 (PMT2).

Referring again to FIG. 2, FIG. 3, FIG. 4A, FIG. 4B and FIG. 4C, at the sub-operation sampling polarized elastic scatter 424 (hereafter "the operation 424"), only S-Polarized total elastic scattered light (i.e., the S-Polarized light directed by the beam splitter 210 through the polarizer 212) is sampled by the first detector channel 214 (PMT1).

Referring again to FIG. 2, FIG. 3, FIG. 4A, FIG. 4B and FIG. 4C, at the sub-operation identifying when aerosol particles are traversing either of the two beams 426 (hereafter "the operation 426"), the difference in intensity of the scattered light in the detector channel that samples elastic scatter polarized in the S direction is used to identify when a particle is traversing through the top and the bottom beams.

Referring to FIG. 4B and FIG. 4C, the oval labeled "B" (428) in FIG. 4B corresponds with the oval labeled "B" (428) in FIG. 4C and indicates that the operations of the method 400 from FIG. 4B continue at the oval labeled "B" (428) in FIG. 4C.

Referring to FIG. 2, FIG. 3, FIG. 4A, FIG. 4B and FIG. 4C, at an operation outputting signals from the detector channels to the computer 430 (hereafter "the operation 430"), signals from the first and second detector channels are output to the computer processor 310 in the data analysis, instrument timing, system control subsystem 108. Generally, signals from the first detector channel 214 (PMT1) and the second detector channel 214 (PMT2), as well as other systems, modules and subsystems of the system 300, are outputted to and received from the computer processor 310 for purposes of performing data analysis, instrument timing and system control operations, by way of the data analysis, instrument timing and system control subsystem 108.

Referring again to FIG. 2, FIG. 3, FIG. 4A, FIG. 4B and FIG. 4C, at an operation determining a ratio of the polarized scatter to the total elastic scatter 432 (hereafter "the operation 432"), the ratio of the polarized elastic scattered light to the total elastic scattered light is calculated by the; computer processor 310, executing program code of the method 400.

Referring again to FIG. 2, FIG. 3, FIG. 4A, FIG. 4B and FIG. 4C, at an operation establishing a threshold for determining if a particle is present in the top beam or the bottom beam 434 (hereafter "the operation 434"), by calculating, in the computer processor 310, the ratio of the signal output from the detector channel that samples elastic scatter polarized in the S direction (i.e., the polarized detector channel) to the total intensity detector, a threshold level is established from which it is determine whether or not the particle and/or particles is/are present in the top beam or the bottom beam and/or traversing the two beams, where the top beam is S-Polarized and the bottom beam is P-Polarized.

Referring to FIG. 2, FIG. 3, FIG. 4A, FIG. 4B and FIG. 4C, at an operation time stamping and assigning velocity to each particle traversing top and bottom beams 436 (hereafter "the operation 436"), as described above, by taking the ratio of the signal output from the first detector channel 214 (PMT1) to the second detector channel 214 (PMT2), thus, establishing the threshold level for determine if the particle is present in the top beam or the bottom beam, a window function is established to match pairs of pulses from the same particle and the time difference between the pulses can be used to measure the velocity of the particle(s) traversing the top and bottom beams. The elastic scatter signal varies as a function of particle size in both the polarized and total intensity detectors in a similar manner, resulting in a fairly constant ratio. Hence this technique can be used for particles of varying sizes and in fact, the total elastic scatter intensity can be used to estimate the size of the particles. Measurements have been conducted on particles of different shapes and absorption characteristics including varying size of polystyrene latex spheres (PSL), silica spheres, bacterial spores and diesel soot and the results show that these parameters do not affect values of the ratio.

Again, referring to FIG. 2, FIG. 3, FIG. 4A, FIG. 4B and FIG. 4C, at an operation performing data analysis, instrument timing, system control functions 438 (hereafter "the operation 438"), as described above, signals from the systems, modules and subsystems of the system 300, are outputted to and received from the computer processor 310 for purposes of performing data analysis, instrument timing and system control operations, by way of the data analysis, instrument timing and system control subsystem 108. In exemplary embodiments, output trigger signals are transmitted to the subsystem 106. Particle classification data can then be used to trigger an electrostatic capture mechanism to deposit individual potential bio-threats particles onto a stainless steel substrate.

At an operation collecting bio-threat aerosol particles in the bio-threat aerosol particle collector 440 (hereafter "the operation 440"), aerosol particles which contain bio-threat elements, determined in the system 200, are collected, based on the output trigger signals, in the bio-threat aerosol particle collector subsystem 106 from the aerosol particle interrogator module 104 after classification of the bio-threat aerosol particles is established in the system 200, implemented the method 400.

Particles that are not classified as targets are discharged with the exiting airflow. Timing and velocity information for each on-the-fly particle are critical for setting an appropriate delay to capture the particles of interest. The electrostatic capture mechanism then electrically charges identified particles and produces a time-delayed electric field to drive them into the stainless steel substrate. The resulting collected sample is highly enriched with target, or potential threat, particles in comparison to their percentage in the ambient air.

An operation return/end 442 (hereafter "the operation 442"), can be iteratively repeated or selectively repeated at any given operation of the method 400, until the operations of the method 400 are completed or the operations can continue until a signal from a user is initiated and/or received causing the system 200 and/or the system 300 and the method 400 to stop and/or end.

Referring to FIG. 2 and FIG. 3 in accordance with exemplary embodiments, the system 200 and the system 300 embody and implement the various methods, procedures, operations and sub-operations of the method 400 in the structure of computer executable program code, computer executable and computer readable media and other hardware, firmware and software modules, network applications and interface platforms, upon which the method 400 is carried out within the technological arts.

Referring to FIG. 3, in accordance with exemplary embodiments, the systems, modules and/or sub-systems of the system 300 can be implemented over a wide area communications network, including an Internet or an extranet or a local area network, including an intranet. The plurality of measuring devices, systems, modules and/or sub-systems of the system 300 can include host computers, storage devices, such as tape drives, disc drives operating individually or in storage library farms.

In exemplary embodiments, the system 200, the system 300 and the method 400 illustrated in FIG. 2, FIG. 3 and FIG. 4A through 4C respectively can be partially and/or fully implemented in software, firmware or hardware or a combination of each. According to exemplary embodiments, the method 400 can be partially and/or fully implemented in software, as executable program code, which comprises an ordered listing of executable instructions for implementing logical functions, and which is executed by either special or general purpose digital computers including a PDA, a personal computer, a workstation, a minicomputer or a mainframe computer, a controller or some other measuring instrumentation.

In exemplary embodiments, the system 200 implements a general purpose digital computer designated as the computer processor 310. The computer processor 310 is a hardware device for executing software implementing the method 400. The computer processor 310 can be any custom made or commercially available, off-the-shelf processor, a central processing unit (CPU), one or more auxiliary processors, parallel processors, graphics processors (or such as graphics processors operating as parallel processors), a semiconductor based microprocessor, in the form of a microchip or chip set, a macroprocesssor or generally any device for executing software instructions. The computer processor 310 can include discrete logic circuits having logic gates for implementing logic functions upon data signals, or the computer processor 310 can include an application specific integrated circuit (ASIC).

In exemplary embodiments, referring to FIG. 3, the computer processor 310 contains memory and storage devices which can include any one of or a combination of volatile memory elements, including random access memory (i.e., including RAM, DRAM, SRAM and/or SDRAM) and non-volatile memory elements including read only memory (i.e., ROM, erasable programmable read only memory, electronically erasable programmable read only memory EEPROM, programmable read only memory PROM, and/or compact disc read only memory CDROM or FLASH memory or cache) magnetic tape, disk, diskette, cartridge, cassette and/or optical memory. The computer processor 310 can have an architecture where various components are situated remotely from one another, but can be accessed by the computer processor 310, either directly and/or locally and/or remotely through/over the various communications networks.

While the exemplary embodiments have been particularly shown and described with reference to preferred embodiments thereof, it will be understood, by those skilled in the art that the preferred embodiments including the first exemplary embodiment, and the second exemplary embodiment have been presented by way of example only, and not limitation; furthermore, various changes in form and details can be made therein without departing from the spirit and scope of the invention. Thus, the breadth and scope of the present exemplary embodiments should not be limited by any of the above described preferred exemplary embodiments, but should be defined only in accordance with the following claim and/or claims and their equivalents. Any and/or all references cited herein are each entirely incorporated by reference herein, including all data, tables, figures, and text presented in the cited references. Also, it is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art. The foregoing description of the specific embodiments will so fully reveal the general nature of the invention that others can, by applying knowledge within the skill of the art, readily modify and/or adapt for various applications such specific embodiments, without undue experimentation, without departing from the general concept of the exemplary embodiments. Therefore, such adaptations and modifications are intended to be within the meaning and range of equivalents of the disclosed embodiments, based on the teaching and guidance presented herein.

What is claimed is:

1. A method of bio-threat detection, using fluorescence interrogation applications, to classify particles traversing top and bottom laser beams in a depolarization velocimetric module having a diode laser source and computer automated instrumentation, the method comprising:
concentrating aerosol particles in a front end aerosol particle concentrator subsystem;
interrogating concentrated aerosol particles, using fluorescence interrogator applications, to classify aerosol particles traversing a top laser beam and a bottom laser beam in the depolarization velocimetric module, wherein interrogating aerosol particles includes:
transmitting a single beam from the diode laser source,
splitting, using a birefringent crystal, the single beam into a plurality of beams each of which having orthogonal polarizations,
directing collected light of the plurality of beams into a first detector channel and a second detector channel,
sampling total elastic scatter in the first detector channel,
sampling polarized elastic scatter in the second detector channel,
identifying, using differences in polarizations of scattered light, when aerosol particles are traversing one of the top laser beam and the bottom laser beam,
determining a ratio of polarized elastic scatter to total elastic scatter,
performing data analysis, instrument timing and system control operations in a data analysis, instrument timing and system control subsystem, using the computer processor for outputting trigger signals to a bio-threat particle collector subsystem, and
collecting bio-threat aerosol particles in the bio-threat particle collector subsystem.

2. The method of claim 1, wherein interrogating aerosol particles further includes determining separation between beams in the plurality of beams.

3. The method of claim 2, wherein determining separation between beams is dependent on characteristics of the birefringent crystal.

4. The method of claim 1, wherein interrogating aerosol particles further includes aligning a group of at least two UV interrogator beams.

5. The method of claim 1, wherein interrogating aerosol particles further includes exciting fluorescence with the group of at least two UV interrogator beams.

6. The method of claim 1, wherein interrogating aerosol particles further includes collecting scattered light with an elliptical reflector.

7. The method of claim 1, further comprising outputting signals from a first photomultiplier tube and a second photomultiplier tube to a computer processor.

8. The method of claim 1, wherein identifying, when aerosol particles are traversing one of the top laser beam and the bottom laser beam, further includes establishing a threshold to determine if a particle is present in one of the top laser beam and the bottom laser beam and time stamping and assigning velocity to each particle traversing one of the top laser beam and the bottom laser beam.

9. A system for bio-threat detection, the system comprising:
a front end aerosol particle concentrator subsystem;
a bio-threat aerosol particle collector subsystem;
a data analysis, instrument timing, and system control subsystem having a computer processor; and
an aerosol particle interrogator module including a depolarization velocimetric system, wherein the depolarization velocimetric system includes:
a diode laser, emitting a single beam for interrogating aerosol particles, communicatively coupled to:
a first lens focusing the single beam emitted from the diode laser,
a one-half waveplate communicatively coupled to:
a first mirror communicatively coupled to:
a cylindrical lens focused to form a sheet beam at a focal volume of an elliptical collection optic,
a second mirror, communicatively coupled between the cylindrical lens and,
a birefringent crystal, which splits the single beam into a group of two orthogonally polarized beams, having a defined separation, and are communicatively coupled to:
an elliptical collection optic reflector residing in an interrogator chamber, wherein the elliptical collection optic reflector collects elastic scattered light from aerosol particles interrogated by a top beam and a bottom beam of the group of two orthogonally polarized beams,
a second lens focusing collected elastic scattered light into detector channels,
a beam splitter, which splits collected elastic scattered light into a first detector channel and a second detector channel, wherein the first and second detector channels include:
a first photomultiplier tube, and
a polarizer that transmits S-polarized light and a second photomultiplier tube, wherein, the first and second photomultiplier tubes output signals to the computer processor, residing in the data analysis, instrument timing, and system control subsystem, and wherein the computer processor executes a plurality of depolarization velocimetric operations and sub-operations.

10. The system of claim 9, wherein the sheet beam formed at the focal volume of the elliptical collection optic has dimensions of about 70 μm by 3 mm.

11. The system of claim 9, wherein the defined separation of the group of two orthogonally polarized beams, is defined by characteristics of the birefringent crystal.

12. The system of claim 11, wherein the defined separation is about 350 μm and wherein the group of two orthogonally polarized beams includes the top beam which is S-polarized and the bottom beam which is P-polarized.

13. The system of claim 9, having the computer processor executing the plurality of depolarization velocimetric operations and sub-operations, includes execution of operations and sub-operations comprising:
splitting the single beam into the group of two orthogonally polarized beams;
determining separation between beams in the group of two orthogonally polarized beams;
aligning a group of at least two UV interrogation beams;

exciting fluorescence with the group of two UV interrogation beams;
collecting scattered light with an elliptical reflector;
directing collected light into the first detector channel and the second detector channel;
sampling total elastic scatter in the first detector channel;
sampling polarized elastic scatter in the second detector channel;
identifying, using differences in polarizations of scattered light, when aerosol particles are traversing one of the top beam of the group of two orthogonally polarized beams for UV interrogation and the bottom beam of the group of two orthogonally polarized beams for UV interrogation by:
  outputting signals from the first photomultiplier tube and the second photomultiplier tube to the computer processor;
  determining a ratio of polarized elastic scatter to total elastic scatter;
  establishing a threshold to determine if a particle is present in one of the top beam of the group of two orthogonally polarized beams and the bottom beam of the group of two orthogonally polarized beams; and
  time stamping and assigning velocity to each particle traversing one of the top beam of the group of two orthogonally polarized beams and the bottom beam of the group of two orthogonally polarized beams;
performing data analysis, instrument timing and system control operations in the data analysis, instrument timing and system control subsystem, using the computer processor;
outputting trigger signals from the computer processor to the bio-threat aerosol particle collector subsystem, and
collecting bio-threat aerosol particles in the bio-threat aerosol particle collector subsystem.

* * * * *